US00PP28803P3

(12) United States Plant Patent
Bernuetz

(10) Patent No.: US PP28,803 P3
(45) Date of Patent: Dec. 26, 2017

(54) *EUPHORBIA* PLANT NAMED 'BONPRI 585'

(50) Latin Name: *Euphorbia pulcherrima* Willd. ex Klotzsch×*Euphorbia cornastra*
Varietal Denomination: Bonpri 585

(71) Applicant: Andrew Bernuetz, Silverdale (AU)

(72) Inventor: Andrew Bernuetz, Silverdale (AU)

(73) Assignee: Bonza Botanicals Pty. Ltd., Yellow Rock, NSW (AU)

( * ) Notice: Subject to any disclaimer, the term of this patent is extended or adjusted under 35 U.S.C. 154(b) by 37 days.

(21) Appl. No.: 14/999,326

(22) Filed: Apr. 25, 2016

(65) Prior Publication Data

US 2017/0311511 P1 Oct. 26, 2017

(51) Int. Cl.
*A01H 5/02* (2006.01)

(52) U.S. Cl.
USPC ..... Plt./302

(58) Field of Classification Search
USPC ..... Plt./302
See application file for complete search history.

*Primary Examiner* — Keith Robinson
(74) *Attorney, Agent, or Firm* — C. A. Whealy

(57) ABSTRACT

A new and distinct cultivar of *Euphorbia* plant named 'Bonpri 585', characterized by its compact, upright and uniformly mounded plant habit; vigorous growth habit; freely branching habit; dark green-colored leaves; freely flowering habit; inflorescences with light pink-colored flower bracts; and good post-production longevity.

1 Drawing Sheet

Botanical designation: *Euphorbia pulcherrima* Willd ex Klotzsch×*Euphorbia cornastra.*

Cultivar denomination: 'BONPRI 585'.

BACKGROUND OF THE INVENTION

The present invention relates to a new and distinct cultivar of *Euphorbia* plant, an interspecific hybrid botanically known as *Euphorbia pulcherrima* Willd. ex Klotzsch×*Euphorbia cornastra*, and hereinafter referred to by the cultivar name 'Bonpri 585'.

The new *Euphorbia* plant is a product of a planned breeding program conducted by the Inventor in Yellow Rock, New South Wales, Australia. The objective of the program is to create and develop new interspecific *Euphorbia* plants with compact, upright and mounded plant habit and attractive flower bracts.

The new *Euphorbia* plant is a naturally-occurring whole plant mutation of *Euphorbia pulcherrima* Willd. ex Klotzsch×*Euphorbia cornastra* 'Bonpripicom', disclosed in U.S. Plant Pat. No. 21,325. The new *Euphorbia* plant was discovered and selected by the Inventor as a single flowering plant from within a population of plants of 'Bonpripicom' in a controlled greenhouse environment in Yellow Rock, New South Wales, Australia on Jun. 13, 2007.

Asexual reproduction of the new *Euphorbia* plant by terminal vegetative cuttings in a controlled greenhouse environment in Yellow Rock, New South Wales, Australia since June, 2007 has shown that the unique features of this new *Euphorbia* plant are stable and reproduced true to type in successive generations of asexual reproduction.

SUMMARY OF THE INVENTION

Plants of the new *Euphorbia* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Bonpri 585'. These characteristics in combination distinguish 'Bonpri 585' as a new and distinct *Euphorbia* plant:

1. Compact, upright and uniformly mounded plant habit.
2. Vigorous growth habit.
3. Freely branching habit.
4. Dark green-colored leaves.
5. Freely flowering habit.
6. Inflorescences with light pink-colored flower bracts.
7. Good post-production longevity.

In side-by-side comparisons conducted in Yellow Rock, New South Wales, Australia, plants of the new *Euphorbia* differ primarily from plants of the mutation parent, 'Bonpripicom' in the following characteristics:

1. Plants of the new *Euphorbia* have a more uniform plant habit than plants of 'Bonpripicom'.
2. Plants of the new *Euphorbia* and 'Bonpripicom' differ in flower bract color as plants of 'Bonpripicom' have red purple-colored flower bracts.

Plants of the new *Euphorbia* can be compared to plants of the *Euphorbia pulcherrima* Willd. ex Klotzsch×*Euphorbia cornastra* 'Bonprilipcom', disclosed in U.S. Plant Pat. No. 21,327. In side-by-side comparisons, plants of the new *Euphorbia* differ primarily from plants of 'Bonprilipcom' in the following characteristics:

1. Plants of the new *Euphorbia* have a more uniform plant habit than plants of 'Bonprilipcom'.
2. Plants of the new *Euphorbia* are more freely branching than plants of 'Bonprilipcom'.
3. Plants of the new *Euphorbia* have smaller and darker green-colored leaves than plants of 'Bonprilipcom'.
4. Plants of the new *Euphorbia* produce more freely flowering than plants of 'Bonprilipcom'.

5. Plants of the new *Euphorbia* had larger inflorescences with larger flower bracts than plants of 'Bonprilipcom'.
6. Plants of the new *Euphorbia* and 'Bonprilipcom' differ in flower bract color as plants of 'Bonprilipcom' have slightly lighter pink-colored flower bracts.
7. Flower bracts of plants of the new *Euphorbia* are more serrate than flower bracts of plants of 'Bonprilipcom'.

BRIEF DESCRIPTION OF THE PHOTOGRAPHS

The accompanying photographs illustrate the overall appearance of the new *Euphorbia* plant showing the colors as true as it is reasonably possible to obtain in colored reproductions of this type. Colors in the photographs may differ slightly from the color values cited in the detailed botanical description which accurately describe the colors of the new *Euphorbia* plant.

The photograph at the top of the sheet comprises a side perspective view of a typical flowering plant of 'Bonpri 585' grown in a container.

The photograph at the bottom of the sheet is a close-up view of a typical inflorescence of 'Bonpri 585'.

DETAILED BOTANICAL DESCRIPTION

Plants used in the aforementioned photographs and described herewith in detail were grown during the autumn in 12-cm containers in an outdoor nursery in Higashiomi, Shiga, Japan and under cultural practices typical of commercial *Euphorbia* production. During the production of the plants, day temperatures averaged 23° C. and night temperatures averaged 13° C. Plants were four months old when the photographs and the description were taken. In the following description, color references are made to The Royal Horticultural Society Colour Chart, Fourth Edition, 2007, except where general terms of ordinary dictionary significance are used.

Botanical classification: *Euphorbia pulcherrima* Willd. ex Klotzsch×*Euphorbia cornastra*. 'Bonpri 585'.

Parentage: Naturally-occurring whole plant mutation of *Euphorbia pulcherrima* Willd. ex Klotzsch×*Euphorbia cornastra* 'Bonpripicom', disclosed in U.S. Plant Pat. No. 21,325.

Propagation:

*Type*.—Terminal vegetative cuttings.

*Time to initiate roots, summer*.—About ten days at 18° C. to 25° C.

*Time to initiate roots, winter*.—About twelve days at 16° C. to 20° C.

*Time to produce a rooted young plant, summer*.—About three weeks at 18° C. to 25° C.

*Time to produce a rooted young plant, winter*.—About four weeks at 16° C. to 20° C.

*Root description*.—Fibrous; white in color.

*Rooting habit*.—Freely branching; medium density.

Plant description:

*Plant habit and form*.—Compact, upright and uniformly mounded plant habit; inverted triangle; inflorescences positioned above the foliar plane; vigorous growth habit.

*Plant height*.—About 21 cm.

*Plant diameter or spread*.—About 34 cm.

*Lateral branch description*.—Blanching habit: Freely branching habit, about six lateral branches develop per plant. Length: About 14 cm. Diameter: About 3.2 mm. Internode length: About 1.9 cm. Aspect: Mostly upright to somewhat outward. Strength: Strong. Texture: Sparsely pubescent. Color: Close to 144A.

*Leaf description*.—Arrangement: Alternate, simple. Length: About 7.5 cm. Width: About 4.3 cm. Shape: Ovate. Apex: Acute. Base: Rounded. Margin: Shallowly serrate; slightly undulate. Venation pattern: Pinnate, reticulate. Texture and luster, upper and lower surfaces: Sparsely pubescent; rugose; matte. Color: Developing leaves, upper surface: Close to 137A. Developing leaves, lower surface: Close to 137D. Fully developed leaves, upper surface: Close to darker than N137A; venation, close to 144B. Fully developed leaves, lower surface: Close to 137B; venation, close to 145C. Petioles: Length: About 2.5 cm. Diameter: About 1.5 mm. Texture, upper and lower surfaces: Pubescent. Color, upper surface: Close to 144A tinged with close to 200C. Color, lower surface: Close to 144A.

Inflorescence description:

*Inflorescence type and habit*.—Inflorescences are compound corymbs of cyathia with numerous flower bracts subtending the cyathia; inflorescences positioned above the foliar plane.

*Quantity of inflorescences*.—Freely flowering habit; about 13 inflorescences develop per plant.

*Inflorescence diameter*.—About 16.5 cm.

*Inflorescence height*.—About 4.6 cm.

*Fragrance*.—None detected.

*Natural flowering season*.—Plants typically flower during the autumn and winter in Japan; inflorescence initiation and development can also be induced under artificial long nyctoperiod and short photoperiod conditions; early flowering habit, plants flower about 50 days under natural season conditions in Japan.

*Post-production longevity*.—Good post-production longevity; plants of the new *Euphorbia* maintain good substance and bract color for about seven weeks.

*Flower bracts*.—Quantity per inflorescence: About 18. Length, largest bracts: About 5.8 cm. Width, largest bracts: About 3.1 cm. Shape: Ovate. Apex: Acuminate. Base: Rounded. Margin: Shallowly serrate. Texture, upper surface: Sparsely pubescent. Texture, lower surface: Pubescent. Aspect: Mostly horizontal. Venation pattern: Pinnate, reticulate. Color: Transitional bracts, upper surface: Close to 62C; towards the apex, close to N137C; margin, proximally, close to NN155B; margin, distally, close to 137C. Transitional bracts, lower surface: Close to 159D; towards the apex, close to 138B; margin, proximally, close to NN155B; margin, distally, close to 143D. Developing bracts, upper surface: Close to 68B; smallest bracts, close to N66A. Developing bracts, lower surface: Close to 155A; smallest bracts, close to 63B. Fully expanded bracts, upper surface: Close to 65B to 65C; margins, close to N155D; venation, close to 152A. Fully expanded bracts, lower surface: Close to 159D; venation, close to 145B. Flower bract petioles: Length: About 1 cm. Diameter: About 1.3 mm. Texture, upper and lower surfaces: Pubescent. Color, upper and lower surfaces: Close to 144B.

*Cyathia*.—Quantity per corymb: About 15. Diameter of cyathia cluster: About 2.9 cm. Height, individual cyathium: About 6 mm. Diameter, individual cyathium: About 6.5 mm. Shape, individual cyathium:

Globose; sessile. Color: Close to 143C; apex, close to 11C to 11D. Nectaries: Quantity per cyathium: One. Size: About 2.2 mm by 3.6 mm. Color: Close to 12A.

*Peduncles*.—Length: About 2.4 mm. Diameter: About 1.9 mm. Strength: Strong. Aspect: Mostly upright. Texture: Smooth, glabrous. Color: Close to N144C.

*Reproductive organs*.—Stamens: Quantity per cyathium: If present, one or two. Stamen length: About 2.3 mm. Filament color: Close to NN155C. Anther shape: Lanceolate. Anther color: Close to 59A. Amount of pollen: None observed. Pistils: Plants of the new *Euphorbia* have not been observed to develop pistils. Seeds and fruits: Seed and fruit production has not been observed on plants of the new *Euphorbia*.

Disease & pest resistance: Plants of the new *Euphorbia* have not been shown to be resistant to pathogens and pests common to *Euphorbia* plants.

Temperature tolerance: Plants of the new *Euphorbia* have been observed to tolerate temperatures ranging from about 8° C. to about 40° C.

It is claimed:

1. A new and distinct *Euphorbia* plant named 'Bonpri 585' as illustrated and described.

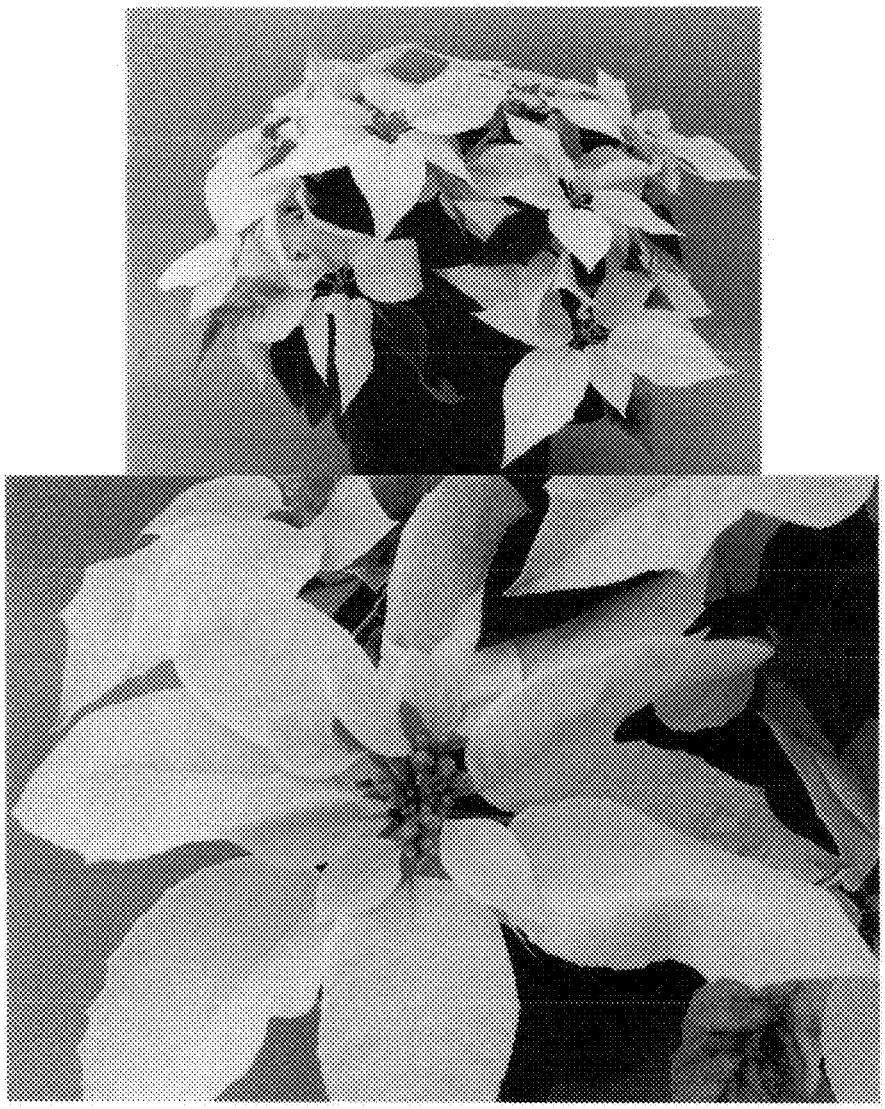

* * * * *